US00PP14487P29

(12) United States Plant Patent
van Rijn

(10) Patent No.: US PP14,487 P2
(45) Date of Patent: Jan. 27, 2004

(54) ANTHURIUM PLANT NAMED 'BRIGHT LOVE'

(50) Latin Name: *Anthurium andreanum*
Varietal Denomination: Bright Love

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/368,868

(22) Filed: Feb. 18, 2003

(51) Int. Cl.[7] ..... A01H 5/00
(52) U.S. Cl. ..... Plt./365
(58) Field of Search ..... Plt./365

*Primary Examiner*—Kent Bell
(74) *Attorney, Agent, or Firm*—C. A. Whealy

(57) ABSTRACT

A new and distinct cultivar of Anthurium plant named 'Bright Love', characterized by its upright and outwardly spreading plant habit; freely clumping growth habit; durable dark green leaves; white, green and red tri-colored spathes with red-colored venation and red-colored spadices that are positioned above and beyond the foliage on strong and erect scapes; freely flowering habit; and good inflorescence longevity.

2 Drawing Sheets

Botanical classification/cultivar designation: *Anthurium andreanum* cultivar Bright Love.

BACKGROUND OF THE INVENTION

The present invention relates to a new and distinct cultivar of Anthurium plant, botanically known as *Anthurium andreanum,* and hereinafter referred to by the name 'Bright Love'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor in May, 1996 of a proprietary selection of *Anthurium andreanum* identified as code number 0040, not patented, as the female, or seed, parent with the *Anthurium andreanum* cultivar Champion, disclosed in U.S. Plant Pat. No. 9,088, as the male, or pollen, parent. The cultivar Bright Love was discovered and selected by the Inventor as a plant within the progeny of the stated cross in a controlled environment in Schipluiden, The Netherlands in July, 1998.

Asexual propagation of the new cultivar by meristem culture in a laboratory in Belgium since August, 1998, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Bright Love. These characteristics in combination distinguish 'Bright Love' as a new and distinct cultivar:

1. Upright and outwardly spreading plant habit.
2. Freely clumping growth habit.
3. Durable dark green leaves.
4. White, green and red tri-colored spathes with red-colored venation and red-colored spadices that are positioned above and beyond the foliage on strong and erect scapes.
5. Freely flowering habit.
6. Good inflorescence longevity.

Plants of the new Anthurium can be compared to plants of the female parent, the proprietary selection identified as code number 0040. In side-by-side comparisons conducted in Schipluiden, The Netherlands, plants of the new Anthurium differed from plants of the selection 0040 in the following characteristics:

1. Plants of the new Anthurium were smaller than plants of the selection 0040.
2. Spathes of plants of the new Anthurium were white, green and red tri-colored whereas spathes of plants of the selection 0040 were red-colored.

Plants of the new Anthurium are most similar to plants of the male parent, the cultivar Champion. In side-by-side comparisons conducted in Schipluiden, The Netherlands, plants of the new Anthurium differed from plants of the cultivar Champion in the following characteristics:

1. Plants of the new Anthurium were more freely clumping than plants of the cultivar Champion.
2. Plants of the new Anthurium had larger leaves than plants of the cultivar Champion.
3. Plants of the new Anthurium had larger spathes than plants of the cultivar Champion.
4. Spadices of plants of the new Anthurium were not as red as spadices of plants of the cultivar Champion.
5. Plants of the new Anthurium were more freely flowering during the winter than plants of the cultivar Champion.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar Bright Love.

The photograph on the second sheet comprises a close-up view of a typical inflorescence of 'Bright Love'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with an average day temperature of 23° C., an average night temperature of 21° C. and light levels about 6 kilolux.

Botanical classification: *Anthurium andreanum* cultivar Bright Love.

Parentage:

*Female parent.*—Proprietary selection of *Anthurium andreanum* identified as code number 0040, not patented.

*Male parent.*—*Anthurium andreanum* cultivar Champion, disclosed in U.S. Plant Pat. No. 9,088.

Propagation:

*Method.*—By meristem culture.

*Time to initiate roots on a meristem-cultured plant.*—About 28 days at 24° C.

*Time to develop roots on a meristem-cultured plant.*—About 270 days at 24° C.

*Root description.*—Thick, fleshy, dark pink to cream-colored; lateral roots, abundant.

Plant description:

*Plant shape.*—Upright and outwardly spreading plant habit, inverted triangle, symmetrical.

*Growth habit.*—Freely clumping, bushy and dense growth habit; about twelve clumps per plant. Appropriate for 14-cm containers; moderately vigorous.

*Plant height, from soil level to top of leaf plane.*—About 38 cm.

*Plant height, from soil level to top of inflorescences.*—About 41 cm.

*Plant diameter or spread.*—About 50 cm.

*Crop time.*—About 10 months are usually required from planting of young plants to finished plants in a 14-cm container.

*Foliage description.*—Arrangement: Alternate; simple. Quantity per plant: About 60. Length: About 12.9 cm. Width: About 8.5 cm. Shape: Deltoid. Apex: Apiculate. Base: Cordate. Margin: Entire; undulate. Texture, upper and lower surfaces: Leather; glabrous, smooth; durable. Venation pattern: Pinnate. Color: Young leaves, upper surface: More green than 144A. Young leaves, lower surface: Between 144A and 146A. Mature leaves, upper surface: Between 139A and 147A. Mature leaves, lower surface: 146A. Venation, upper surface: 144A. Venation, lower surface: 144A to 144B. Petiole: Length: About 25.6 cm. Diameter, just below geniculum: About 4 mm. Diameter, at plant base: About 5 mm. Texture: Smooth. Color: 143B. Geniculum length: About 2.3 cm. Geniculum diameter: About 4.5 mm. Geniculum color: 144A to 144B. Wing length: About 2.6 cm. Wing diameter: About 4.5 mm. Wing color: N170C to N170D.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about five inflorescences per plant. Inflorescences not fragrant.

*Inflorescence longevity.*—Inflorescences last about two months under winter conditions and about three months under summer conditions; inflorescences persistent.

*Spathe.*—Length: About 6 cm. Width: About 7.6 cm. Depth: About 6.4 cm. Shape: Reniform. Apex: Mucronulate. Base: Cordate. Margin: Entire. Texture, upper and lower surfaces: Leathery; glabrous, smooth. Aspect: Moderately cupped. Color: When opening, front surface: 155A; towards the base, 157D. When opening, back surface: 157A to 157B; towards the base, 145C to 145D. Fully developed, front surface: Ground color, 155A; interveinal areas, 145A to 145B; midvein and immediate surrounding area, 49B to 49C; primary veins, 51B. Color becoming closer to 144A to 144B; midvein and immediate surrounding area, 53D. Fully opened, back surface: Ground color, 155A; towards the margins, 145A; midvein and immediate surrounding area, 48D; primary veins, 51B.

*Spadix.*—Length: About 4.8 cm. Diameter: About 7 mm. Shape: Columnar, tapering towards the apex; apex, obtuse. Cross section: Rounded. Aspect: About 10° from vertical. Color: Immature: 51A; towards the apex, 181D. Mature: 51C; towards the apex, 53A.

*Flowers.*—Quantity per spadix: Numerous, about 250. Shape: Rounded. Height: Less than 0.5 mm. Diameter: About 0.8 mm.

*Reproductive organs.*—Androecium: Anther color: 11D. Amount of pollen: Moderate. Pollen color: 11C. Gynoecium: Stigma shape: Ovoid. Stigma color: N155D. Ovary color: N155D.

*Scape.*—Length: About 29.4 cm. Diameter: About 3.5 mm. Strength: Strong. Aspect: Erect to slightly outwardly slanted, about 30° from vertical. Color: 144A.

*Seed and fruit.*—Seed and fruit development has not been observed on plants of the new Anthurium.

Disease/pest resistance: Under commercial production conditions, plants of the new Anthurium have not been observed to be resistant to pathogens or pests common to Anthurium.

Temperature tolerance: Plants of the new Anthurium have been observed to tolerate temperatures from 14 to 35° C.

It is claimed:

1. A new and distinct cultivar of Anthurium plant named 'Bright Love', as illustrated and described.

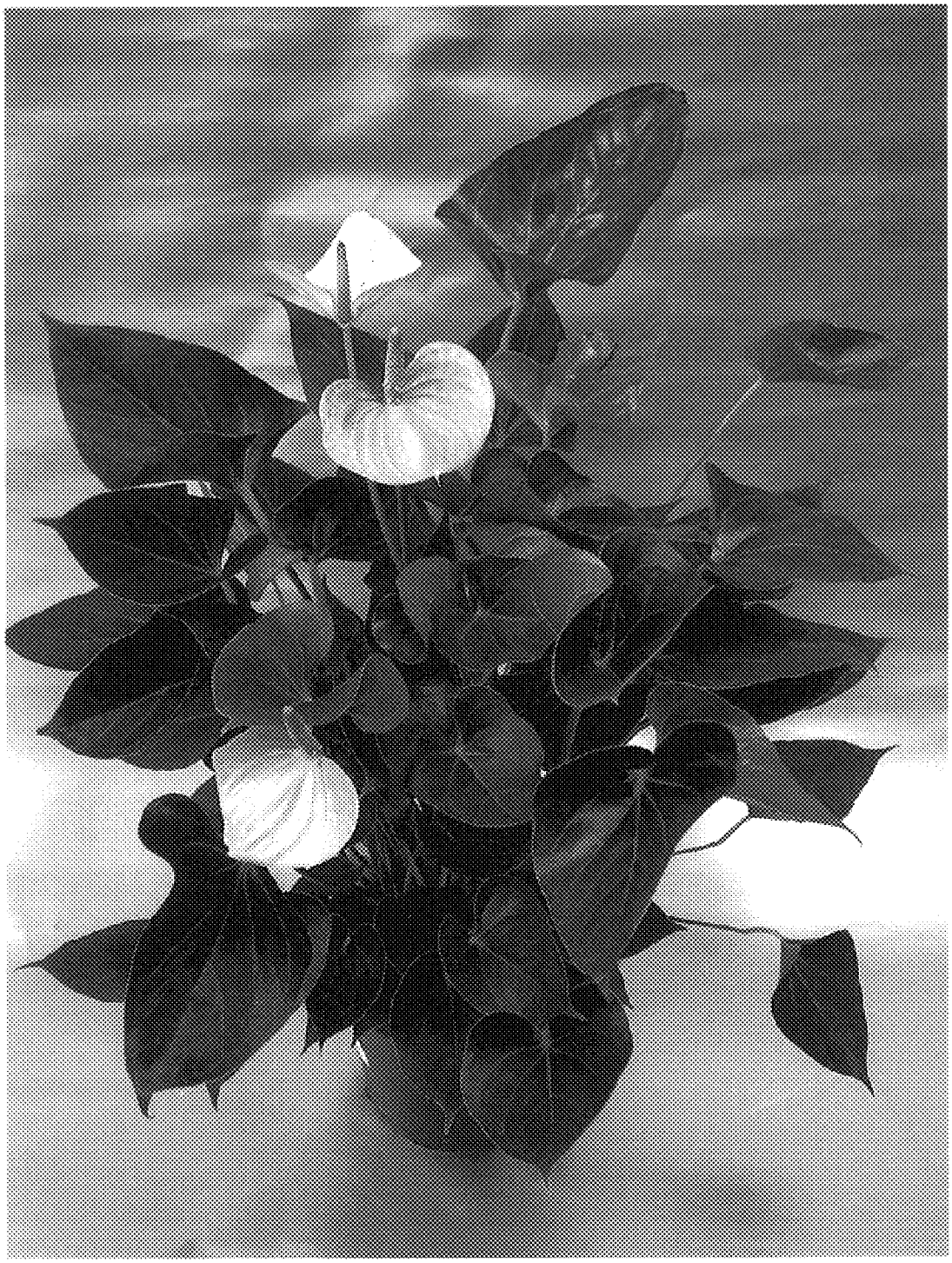

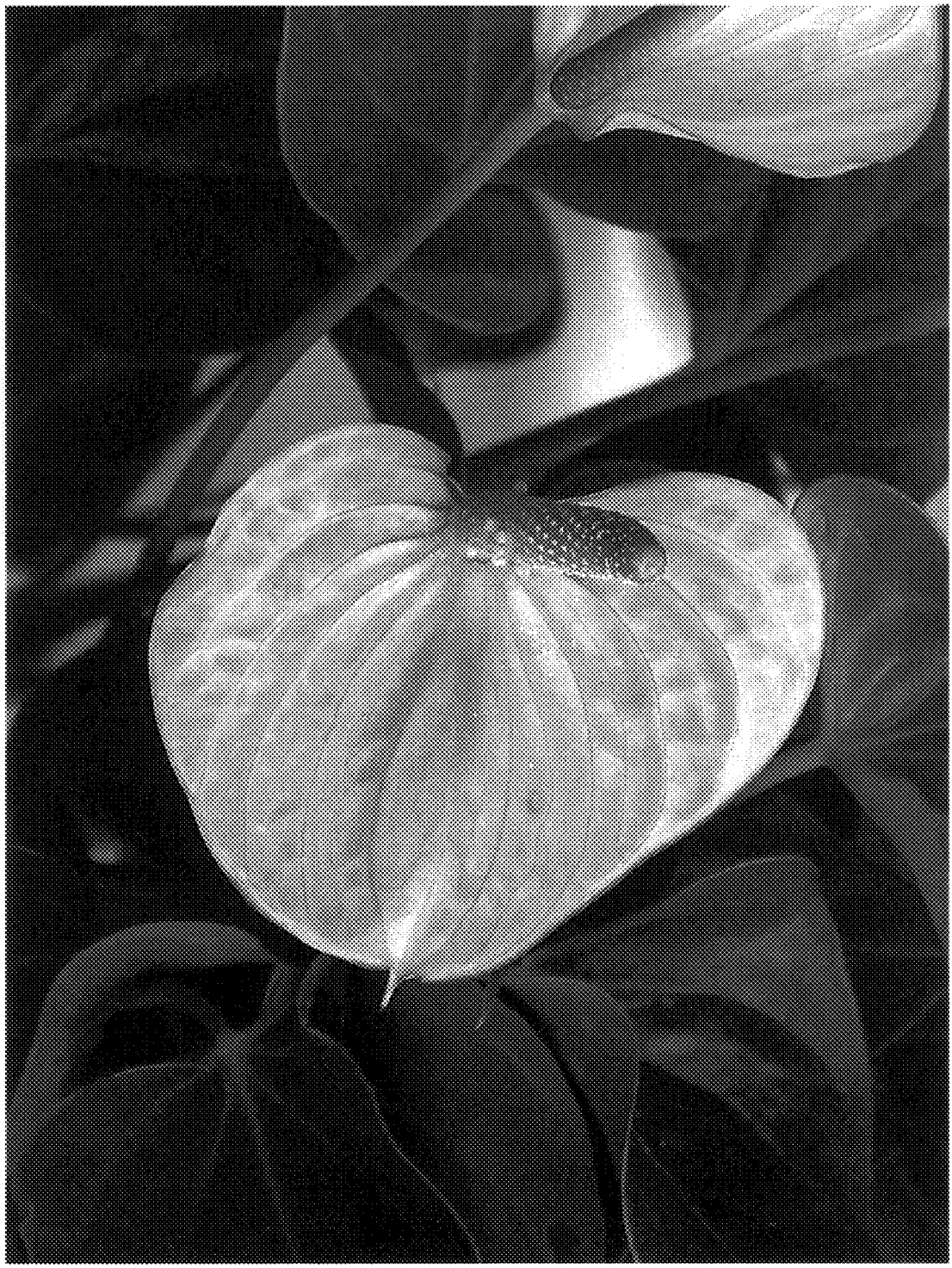

* * * * *